US010271889B2

(12) United States Patent
Bronskill et al.

(10) Patent No.: US 10,271,889 B2
(45) Date of Patent: Apr. 30, 2019

(54) APPARATUS AND METHOD FOR COOLING A TISSUE VOLUME DURING THERMAL THERAPY TREATMENT

(75) Inventors: Michael J. Bronskill, Toronto (CA); Rajiv Chopra, Toronto (CA)

(73) Assignee: Sunnybrook Health Sciences Centre, Toronto, ON (CA)

( * ) Notice: Subject to any disclaimer, the term of this patent is extended or adjusted under 35 U.S.C. 154(b) by 168 days.

(21) Appl. No.: 12/824,226

(22) Filed: Jun. 27, 2010

(65) Prior Publication Data

US 2011/0319748 A1   Dec. 29, 2011

(51) Int. Cl.
*A61F 7/12* (2006.01)
*A61N 7/02* (2006.01)
*A61B 18/00* (2006.01)
*A61B 90/00* (2016.01)

(52) U.S. Cl.
CPC .............. *A61B 18/00* (2013.01); *A61F 7/12* (2013.01); *A61B 2018/00023* (2013.01); *A61B 2018/00547* (2013.01); *A61B 2018/00744* (2013.01); *A61B 2018/00791* (2013.01); *A61B 2090/374* (2016.02); *A61N 7/022* (2013.01)

(58) Field of Classification Search
CPC ................ A61F 7/12; A61F 2007/0028; A61F 2007/0056; A61B 2018/0023; A61B 2018/00547; A61B 18/00
USPC ......................................................... 607/105
See application file for complete search history.

(56) References Cited

U.S. PATENT DOCUMENTS

| 787,920 | A | * | 4/1905 | Hofmann | 607/105 |
|---|---|---|---|---|---|
| 4,841,970 | A | * | 6/1989 | Rand | 607/113 |
| 4,844,073 | A | * | 7/1989 | Pohler | 607/113 |
| 5,417,721 | A | * | 5/1995 | Mallasch | 607/108 |
| 5,474,071 | A | * | 12/1995 | Chapelon et al. | 600/439 |
| 5,649,973 | A | * | 7/1997 | Tierney et al. | 607/101 |
| 5,800,485 | A | * | 9/1998 | Trop et al. | 607/105 |
| 6,009,351 | A | * | 12/1999 | Flachman | 607/101 |
| 6,071,238 | A | * | 6/2000 | Chapelon et al. | 600/439 |
| 6,159,207 | A |   | 12/2000 | Yoon | |
| 6,224,590 | B1 |   | 5/2001 | Daikuzono | |
| 6,517,562 | B1 | * | 2/2003 | Holland | 606/197 |
| RE38,143 | E | * | 6/2003 | Tierney et al. | 607/101 |
| 6,575,969 | B1 |   | 6/2003 | Rittman, III et al. | |
| 7,077,858 | B2 |   | 7/2006 | Fletcher et al. | |
| 7,101,387 | B2 |   | 9/2006 | Garabedian et al. | |
| 7,125,407 | B2 |   | 10/2006 | Edwards et al. | |

(Continued)

*Primary Examiner* — Kaitlyn E Smith
(74) *Attorney, Agent, or Firm* — Intrinsic Law Corp.

(57) ABSTRACT

An apparatus for cooling certain tissues in the vicinity of diseased or other tissue undergoing thermal treatment is disclosed. The present apparatus is configured and designed to have certain physical characteristics, e.g., certain acoustic and imaging responses. In some embodiments the present apparatus is compatible with magnetic resonance imaging (MRI) environments used in conjunction with the thermal treatment, or other imaging environments. In some embodiments the present apparatus is detectable by said MRI and is within the imaging field of view (FOV) but causes few or no imaging artifacts. Additionally, the present apparatus does not substantially interfere with the thermal treatment, e.g., ultrasonic therapy, which can proceed to heat the targeted volume of tissue while protective cooling of tissues near the diseased tissue by the present apparatus takes place.

22 Claims, 6 Drawing Sheets

(56) References Cited

U.S. PATENT DOCUMENTS

| | | |
|---|---|---|
| 7,243,655 B2 | 7/2007 | Gonzales |
| 7,326,195 B2 | 2/2008 | Willard et al. |
| 7,326,235 B2 | 2/2008 | Edwards |
| 7,344,529 B2 | 3/2008 | Torchia et al. |
| 7,387,638 B2 * | 6/2008 | Gonzales ............ 607/96 |
| 7,480,533 B2 | 1/2009 | Cosman et al. |
| 7,485,109 B2 | 2/2009 | Willard et al. |
| 7,491,223 B2 | 2/2009 | Lasheras |
| 2002/0010502 A1 * | 1/2002 | Trachtenberg ............ 607/102 |
| 2002/0116041 A1 * | 8/2002 | Daoud ............ 607/105 |
| 2003/0069619 A1 * | 4/2003 | Fenn et al. ............ 607/101 |
| 2003/0144593 A1 * | 7/2003 | Whitmore et al. ............ 600/459 |
| 2004/0024434 A1 * | 2/2004 | Yang et al. ............ 607/96 |
| 2005/0177209 A1 | 8/2005 | Leung et al. |
| 2006/0142826 A1 | 6/2006 | Willard et al. |
| 2007/0239062 A1 * | 10/2007 | Chopra et al. ............ 600/549 |
| 2008/0033471 A1 * | 2/2008 | Paz et al. ............ 606/190 |
| 2008/0161785 A1 | 7/2008 | Crowe et al. |
| 2008/0215042 A1 | 9/2008 | Swanson |
| 2008/0275306 A1 | 11/2008 | Rebuffat et al. |
| 2009/0018446 A1 * | 1/2009 | Medan et al. ............ 600/439 |
| 2009/0157070 A1 * | 6/2009 | Oskin et al. ............ 606/33 |
| 2009/0171157 A1 * | 7/2009 | Diederich et al. ............ 600/116 |
| 2011/0178391 A1 * | 7/2011 | Fernandez et al. ............ 600/411 |
| 2012/0101412 A1 * | 4/2012 | Vortman et al. ............ 601/3 |
| 2012/0253097 A1 * | 10/2012 | Shohat et al. ............ 600/1 |
| 2012/0323296 A1 | 12/2012 | Takeda et al. |

\* cited by examiner

APPARATUS AND METHOD FOR COOLING A TISSUE VOLUME DURING THERMAL THERAPY TREATMENT

TECHNICAL FIELD

The present disclosure generally relates to devices for thermal treatment of diseased tissues. More specifically, the present disclosure relates to devices and ways to cool tissue in the vicinity of the diseased tissue being treated by said thermal treatment.

BACKGROUND

Thermal coagulation therapy may be used for the treatment of localized diseased tissue, e.g., tumors, in a diseased organ or body. Generally, a target volume of tissue is sufficiently heated to achieve a therapeutic effect, such as thermal coagulation. Tissue thermal coagulation depends on a number of factors, and temperatures in the range of 55-60° C. are generally considered sufficient to provide enough energy to cause such coagulation. Cell death results from heating to these temperatures, and a region of irreversible thermal damage can be observed with imaging following the treatment. In addition, heating can be produced from minimally-invasive applicators, eliminating the need for open surgery, and potentially reducing recovery time and morbidity for patients. This approach has been used with some success in the treatment of isolated primary liver cancers and colorectal metastases for patients otherwise ineligible for surgery.

Interstitial thermal therapy is currently practiced by inserting heating applicators directly into a target site within an organ. Several energy sources have been integrated into interstitial heating applicators, including lasers, ultrasound, microwave, and radiofrequency energy. Preferably, interstitial thermal therapy delivers sufficient thermal energy to coagulate an entire target volume, while avoiding undesirable thermal damage to adjacent normal tissues. This strategy is referred to as "conformal thermal therapy." One limitation of present interstitial thermal therapy technology is the inability to control or adjust the three-dimensional pattern of energy deposition dynamically during a treatment. Most current applicators act as point or line sources of energy resulting in patterns of energy deposition in tissue which are highly symmetrical about the active portion of the applicator. This makes it difficult to treat targets with complex geometry accurately, and does not take full advantage of the imaging information available with imaging technology such as magnetic resonance imaging (MRI).

One application of interstitial heating is transurethral prostate thermal therapy, which selectively coagulates diseased prostate tissue using a device located within the prostatic urethra, and minimizes harm to adjacent normal tissues such as the rectal and bladder walls. Disease targets include prostate cancer and benign prostatic hyperplasia (BPH). It is difficult for current transurethral thermal therapy technologies to produce a thermal treatment (cell death) pattern that conforms accurately to the geometry of the prostate gland or to targeted sub-regions of the prostate gland.

In conformal prostate thermal therapy applications, it is often desirable to implement some form of quantitative temperature monitoring for feedback during treatment to ensure accurate delivery of energy to the prostate gland. Temperature monitoring of treated (or heated) tissue regions can be accomplished in several ways. These include direct measurements as well as indirect measurements of the spatial and/or temporal thermal field in the treatment region.

Magnetic resonance imaging ("MRI") has been used to measure spatial heating patterns non-invasively in tissue. Several MRI techniques are available to measure the temperature distribution in tissue. These techniques are mainly possible because of the temperature dependence of various nuclear magnetic resonance ("NMR") biophysical parameters such as T1, T2, diffusion, magnetization, and proton resonant frequency. The most commonly used technique for measuring temperature in MRI-guided thermal therapy is the proton resonant frequency ("PRF") shift technique, which exploits the direct proportionality between the resonant frequency of water protons and temperature. A common technique to measure this effect employs the subtraction of a baseline phase image obtained prior to heating from a phase image obtained during heating to measure the change in phase resulting from local temperature elevations. The change in phase can then be related to the change in temperature through the expression, $$\Delta T(x, y) = \frac{\Delta \Phi_t}{\alpha \cdot \gamma \cdot B_o \cdot TE}$$

$\Delta T$ is the temperature change between two images, $\Delta \Phi_t$ is the phase change due to temperature differences between the same two images, $\alpha$ is the proton resonant frequency shift coefficient (typically −0.01 ppm/° C.), $\gamma$ is the gyromagnetic ratio, $B_o$ is the strength of the main magnetic field (T), and TE is the echo time of the imaging sequence used to acquire the two images.

In performing thermal treatments as described above, it is usually preferable to avoid damage to normal (non-diseased) tissue due to heating of the normal tissue in the vicinity of the diseased tissue. This is of special concern for normal tissues proximal to or in the vicinity of the treatment area (sometimes called a target volume or treatment zone) where heat is applied to the diseased tissue. In the example of thermal treatment of the prostate, ultrasound, electromagnetic, RF, microwave, and other sources of heat can lead to heating of normal (non-diseased) tissue surrounding the prostate or adjacent thereto, for example the tissue of the rectum or rectal walls. Excessive heating of this normal tissue could cause unwanted damage to the normal tissue, which could contribute to patient morbidity.

Various attempts to prevent over-heating of tissue outside the targeted diseased tissue have included attempts to confine the volume within which the thermal therapy is applied so that thermal effects are reduced beyond the localized volume being treated. This solution can result in slower or less effective treatment, as treatment of an extended region in space would require application of many such localized treatments to a small treatment zone to avoid spreading the thermal energy to normal tissues outside the treatment zone. Other attempts to account for the heating of normal tissues outside a target volume use the cooling effects of time so that short duration pulses of heat are applied to a target area in order to avoid over-heating of various locations and to enable conduction or other heat transfer mechanisms to keep the temperature of normal tissues in check. Yet other attempts to counter the effect above include using the heat transfer capabilities of perfused tissue having blood flowing therethrough to carry away certain doses of heat applied to the tissue.

Therefore, it remains needed or useful to develop techniques and treatment systems to heat the diseased tissues in a targeted treatment volume sufficiently while at the same time avoiding over-heating of the proximal tissues and organs. In particular, the present embodiments and concepts will illustrate to one skilled in the art methods and apparatus for achieving an effective, robust, efficient thermal treatment of diseased tissue simultaneously with no, little, or reduced risk of damage to nearby normal tissues and organs under given conditions.

SUMMARY

Embodiments of the present apparatus and method for use are provided below. It is understood that the present preferred embodiments are given for the purpose of illustration and explanation of the nature of the inventions herein, and not by way of limitation of the scope of the inventions. The same or similar methods and apparatus as described herein can be used in the context of thermal treatment of other organs, especially those where the treatment is near or adjacent to a cavity in the body.

Some embodiments are directed to an apparatus for use in conjunction with thermal therapy treatment of a patient, including an elongated member body adapted in shape and size for inclusion at least in part into a body cavity of the patient, said elongated member generally having a first end inserted into the patient's cavity and a second end generally opposing said first end; at least one ingress and one egress path for a cooling fluid so that said fluid may pass into said apparatus through said ingress path and said fluid may pass out of said apparatus through said egress path; said elongated member further comprising a housing compatible with a thermal therapy modality and further compatible with an imaging modality.

Other embodiments are directed to system for controlling a temperature of a healthy tissue volume of a patient during thermal therapy treatment of a diseased tissue volume of said patient proximal to said healthy tissue volume, including an elongated member, adapted in shape and size for inclusion at least in part into a body cavity of the patient, said member comprising a housing compatible with a thermal therapy modality of said treatment and further compatible with a treatment imaging modality; said elongated member comprising cooling fluid inlet and fluid discharge ports through which a cooling fluid may flow; said elongated member further comprising a fluid plenum proximal to a first end of said member, and proximal to said healthy tissue volume, said plenum allowing receipt of and discharge of said cooling fluid therethrough; a fluid flow control apparatus for controlling a flow property of said cooling fluid into said inlet port and out of said discharge port; and a fluid temperature control apparatus for monitoring and controlling a thermal property of said cooling fluid so as to maintain a temperature of said healthy tissue volume within an accepted range of temperatures.

The present disclosure also teaches ways, techniques and methods for controlling a temperature of a healthy tissue volume during thermal therapy treatment of nearby unhealthy tissue volumes, including by making and applying the above apparatus in a patient, and more specifically, in a body cavity (e.g., the rectum) of a patient.

BRIEF DESCRIPTION OF THE DRAWINGS

For a fuller understanding of the nature and advantages of the present invention, reference is be made to the following detailed description of preferred embodiments and in connection with the accompanying drawings, in which.

DETAILED DESCRIPTION

Figure 1:
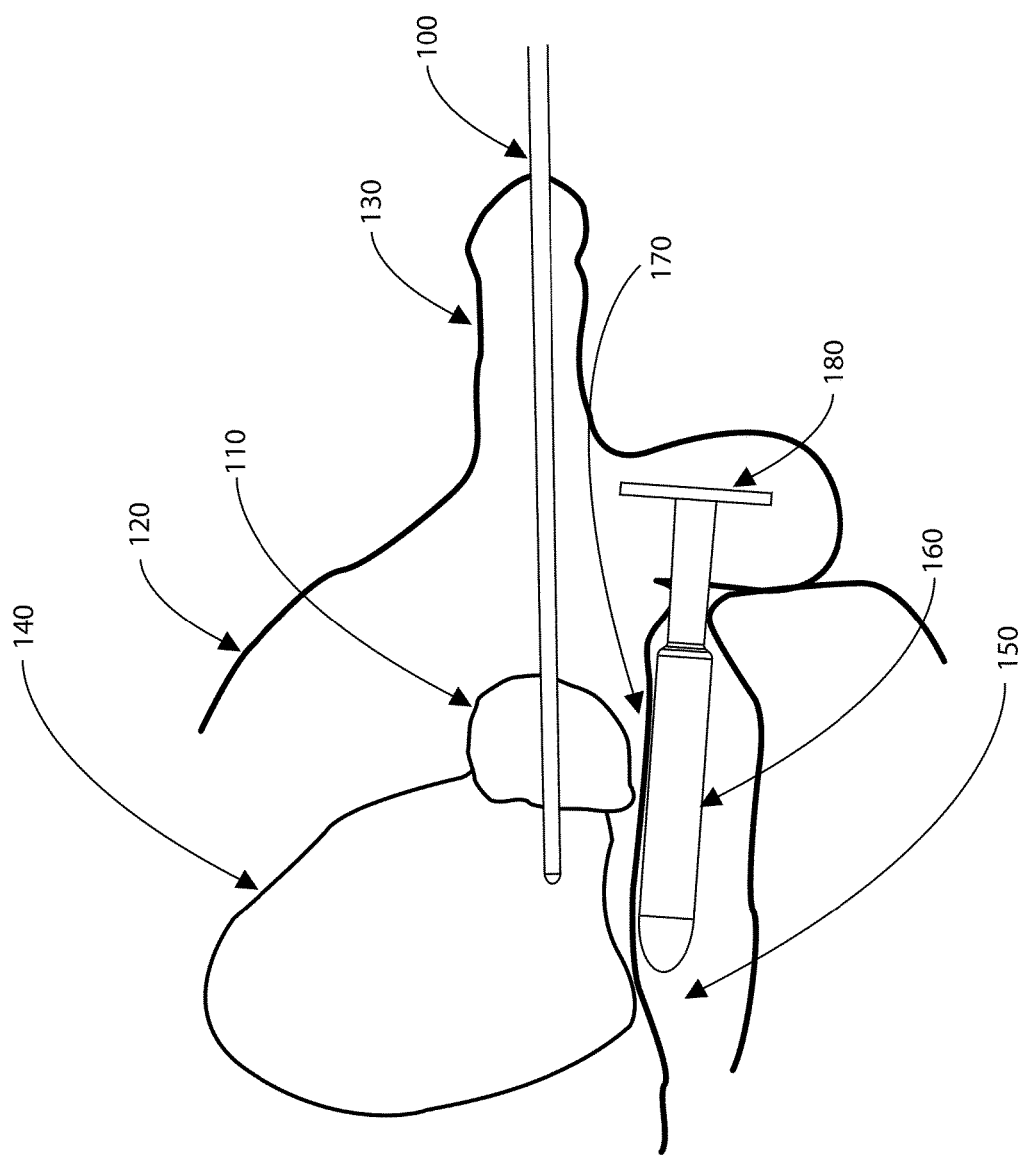
FIG. 1 illustrates an exemplary cross-section of a patient undergoing prostate thermal treatment, including exemplary placement of a heating treatment apparatus and a cooling apparatus.

As discussed above, thermal treatment of diseased tissue, e.g., by ultrasonic heating, has been used and proposed for use in therapy to treat various conditions. In one example, ultrasound heating of the male prostate is to be used to treat diseases such as prostate cancer by thermal coagulation of the diseased tissue or tumor. The present techniques and apparatus should be considered capable of treating conditions beyond just prostate cancer of course, including treating other conditions of the male prostate, e.g., benign prostate hyperplasia ("BPH"). Also, other male and/or female reproductive organ conditions may be treated hereby, and other organs, and conditions as well, such as tumors of the breast, brain and other internal organs, which will be understood by those skilled in the art.

Improved techniques and apparatus have been presented by the present inventors, for example in U.S. patent application Ser. No. 11/076,669 entitled "Treatment of Diseased Tissue Using Controlled Ultrasonic Heating," and application Ser. No. 11/728,778 entitled "Method and Apparatus for Obtaining Quantitative Temperature Measurements in Prostate and Other Tissue Undergoing Thermal Therapy Treatment," which are incorporated herein by reference. The present apparatus and methods can be applied in some embodiments to the circumstances given in these references and to other situations where ultrasonic or other localized energy is used to provide heating of a diseased tissue and MRI or other imaging is used to detect the result of the thermal treatment and/or guide the same. In these cases, special attention would need to be paid to the construction and placement of any device in or near the body for cooling of tissue that is to be protected during the thermal treatment.

More specifically, the apparatus used for such cooling should be designed and constructed in order to avoid or minimize the following potential consequences: (1) the introduction of distortions or artifacts into the MRI or other imaging results, and (2) interference with the localized acoustic or equivalent energy field used to provide the heating of the diseased region. If the construction, placement, operation, or materials used are not suitable, image artifacts can result, damage to adjacent tissues can occur, and/or reflections or scattering or other absorption effects can disrupt the acoustic beam used to heat the diseased tissue. In addition to the above consequences, damage to the cooling apparatus itself could result if the apparatus itself is subjected to and takes in an excessive amount of heat during the thermal treatment process.

An apparatus for cooling certain tissues in the vicinity of diseased tissue undergoing thermal treatment is disclosed herein. The present apparatus is configured and designed to have certain physical characteristics, e.g., certain acoustic and imaging responses. In some embodiments the present apparatus is compatible with magnetic resonance imaging environments used in conjunction with the thermal treatment, or similar imaging environments. In some embodiments the present apparatus is detectable by said MRI and is within the imaging field of view (FOV) but causes few or no imaging artifacts. Additionally, the present apparatus does not substantially interfere with the energy deposition of the thermal treatment, e.g., ultrasonic therapy, which can proceed to heat the diseased tissue while thermal protection of tissues near the diseased tissue by the present apparatus takes place.

FIG. 1 illustrates an exemplary treatment apparatus 100 consistent with the present teachings to treat a condition of the male prostate 110 in a patient 120, e.g., prostate cancer. In this illustrative cross-section, the treatment apparatus 100 includes a source of heating (e.g., an ultrasound source) capable of elevating the temperature of some parts of prostate 110 to temperatures useful for affecting a desired treatment outcome. In some embodiments, the treatment outcome includes heating the target tissue to above a certain threshold temperature to achieve a biological effect such as coagulation or cell death. In some embodiments, the treatment outcome includes achieving a desired thermal dose, as understood by those skilled in the art, to a degree capable of causing cell death in a target region of diseased tissue. In some embodiments, the treatment outcome includes achieving a given threshold of temperature and thermal dose.

The treatment apparatus 100 can deliver its heat to the target diseased tissue continuously or in pulsed form, and by electrically and/or mechanically scanning the target tissue volume so as to accomplish the desired treatment outcome. In some embodiments a conformal coverage of a three-dimensional treatment volume can be accomplished using a driven ultrasound array mounted on or in treatment apparatus 100. Other patents and patent applications, such as those cited above by the present inventors, incorporated herein by reference, describe ways of targeting select regions of tissue for thermal treatment and other steps taken in this regard, including thermometry and control of treatment apparatus 100.

The target volume in which the heating takes place can include substantially the entire prostate 110 if appropriate, or it can include a portion of prostate 110. For example, the thermal treatment can be limited to only those portions of prostate 110 which are affected by prostate cancer. In some embodiments, treatment apparatus 100 comprises one or more ultrasonic energy sources which radiate their energy through an appropriate acoustic window disposed on one or more sides of the treatment apparatus 100.

Treatment apparatus 100 can be inserted into the body of a male patient 120 through the patient's penis 130 (through the urethra), and may extend into the bladder 140. The bladder may be emptied or depressurized of its contents through appropriate fluid flow channels appropriately disposed within treatment apparatus 100 as described in the above references for example.

The following discussion addresses elimination or reduction of the risk of thermal damage to normal tissues lying near the target treatment volume such as those described above. In some examples, heat energy is transmitted by treatment apparatus 100 in a direction that would tend to heat the patient's rectum 150. Specifically, if heat energy is delivered by treatment apparatus 100 in a direction downward with respect to the drawing of FIG. 1, this heat can reach the rectum wall 170 in the vicinity of the prostate 110 and cause burns or otherwise damage tissue that should not be subjected to heat from the thermal treatment process.

Accordingly, a cooling apparatus 160 can be inserted into the rectum 150 using an external portion 180 to counter the effects of heating at or near the rectum 150. The cooling apparatus 160 can take many shapes, forms, sizes, and configurations. FIG. 1 only illustrates a representative cooling apparatus 160, and further details and embodiments of such an apparatus are given below.

Figure 2:
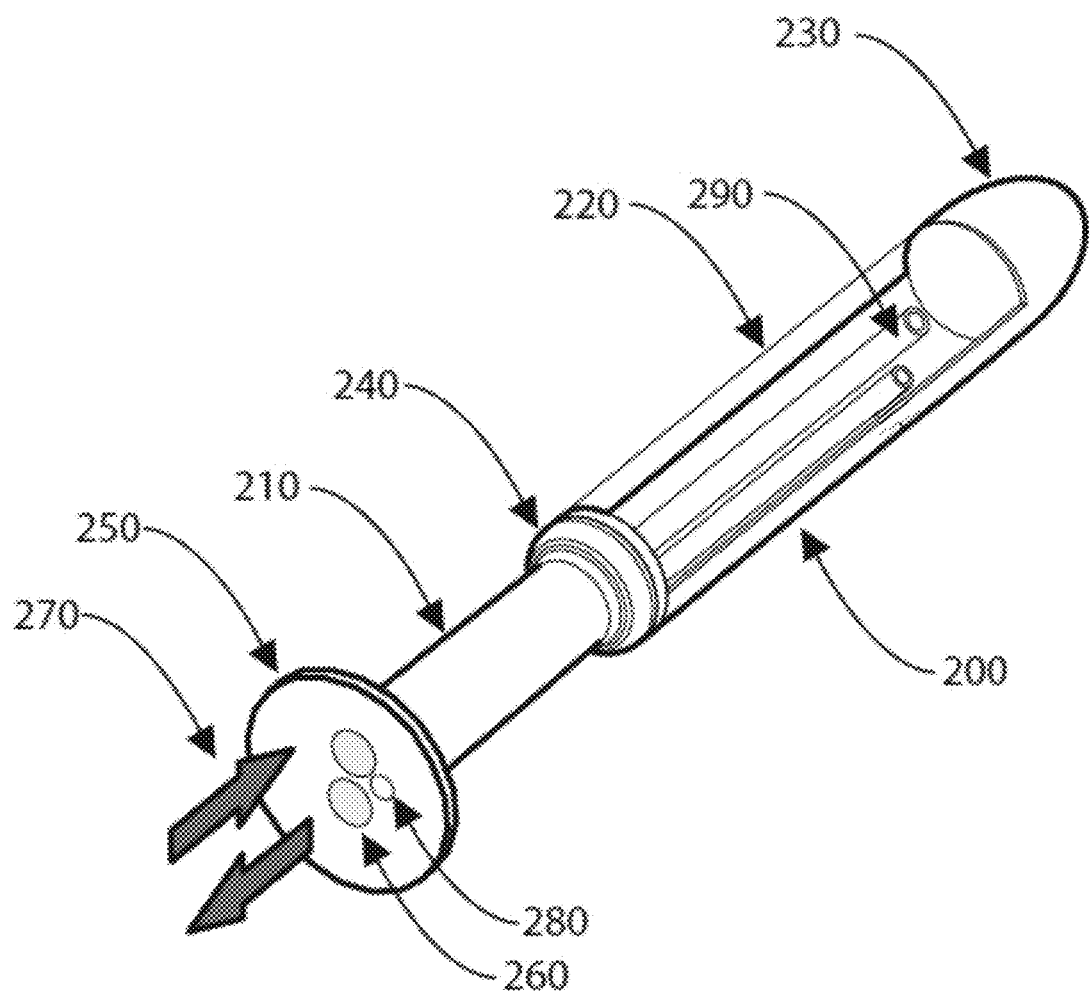
FIG. 2 illustrates a perspective view of an exemplary cooling apparatus according to one or more preferred embodiments.

FIG. 2 illustrates an exemplary embodiment of a cooling apparatus 200, which may in some embodiments be equivalent or similar in use to the cooling apparatus 160 described earlier. Cooling apparatus 200 is used for countering, negating, reducing, or mitigating the effects of an adjacent thermal treatment process on non-diseased portions of the body or portions of the body to be protected from thermal effects of a thermal treatment.

In some embodiments, cooling apparatus 200 comprises an elongated portion 220 which can be several inches in length. A first tip end 230 of cooling apparatus 200 enables insertion of said apparatus into a body cavity, for example the rectum of the patient, and may be tapered, rounded or pointed at said first end 230 to accomplish this purpose. The first tip end 230 of cooling apparatus 200 may be manufactured of a solid plastic for example. A second taper 240 may couple the cooling section 220 of cooling apparatus 200 with the elongated portion 210 which passes through the patient's anus. Patient comfort and the engineering design of the apparatus 200 are taken into consideration in selecting the lengths and diameters of the various portions of cooling apparatus 200.

Cooling apparatus 200 may comprise thin plastic walls, e.g., made of a thin plastic material that can hold the cooling water within apparatus 200 but cause minimal absorption, reflection or scattering of an ultrasound heating field used in the thermal treatment. In use, the cooling apparatus 200 is inserted an appropriate depth into the rectum of a prostate patient and a fluid is made to flow therein when appropriate to reduce or control the temperature of the tissue near the cooling apparatus 200. In some embodiments, the cooling apparatus 200 is placed in contact with a rectal wall area of the patient to prevent unwanted heating of the rectal wall tissue during thermal treatment of the nearby prostate.

Running along the length of cooling apparatus 200 are one or more fluid channels that permit circulation of a cooling fluid into and out of the cooling apparatus. In FIG. 2, as an exemplary embodiment, a second end 250 of the apparatus is equipped with a pair of openings 260, one for ingress of cooling fluid and the other for egress of cooling fluid. A plenum 290 can be included and numerous flow-paths may be provided to cool the patient at certain locations using the cooling apparatus 200. Cooling fluid is illustrated as entering and exiting the second end 250 by the arrows 270 in the present simplified drawing.

Also running into the apparatus 200, for example in separate channels 280 or sleeves are one or more sensors and/or conductors coupled to sensors within the cooling apparatus 200. One type of sensor disposed within cooling apparatus 200 is a fiber-optic temperature sensor, which is compatible with MRI. During treatment, the temperature sensor could sense a temperature of the tissue being protected from over-heating by cooling apparatus 200. In some embodiments, the temperature sensor is disposed within or near the tip end 230 of cooling apparatus 200. Prior to the flow of any cooling fluid within the cooling apparatus 200, the temperature sensor could also enable calibration of the baseline temperature for the PRF temperature-measuring method of MRI.

The cooling fluid may be a gas or a liquid. In certain embodiments, the cooling fluid is liquid water, e.g., sterile, pure or de-ionized laboratory water, or a saline solution or other salt solution, provided at or to second end 250 by a supply system. The cooling fluid may be provided with characteristics conducive to best operation in an acoustic heating and/or MRI imaging environment. For example, the cooling fluid (for example water) can be provided as a fluid with acoustic impedance (generally, speed of sound, density) properties similar to those of surrounding tissue to minimize the reflection, scattering or other disruption to an ultrasonic heating beam or sound field. In addition, in some embodiments it is preferred to employ a cooling fluid which substantially does not absorb the incident ultrasound energy and therefore does not experience intrinsic heating by the ultrasound field. The design of the cooling system and the thermal treatment system may be such that it is preferable that the cooling fluid and the cooling apparatus 200 do not reflect or scatter an appreciable amount of acoustic radiation so as not to disrupt the acoustic field set up for treatment of the diseased tissue volume. The use of polymeric, plastic, rubber, membrane, or other materials based on their relative acoustic impedance matching to the cooling fluid and surrounding tissues can be a way to enhance the utility of the present apparatus in an acoustic environment such as that used in ultrasonic thermal therapy of the prostate.

Furthermore, the cooling fluid may be doped with a material to be compatible with the imaging system used to monitor the thermal treatment. Dissolved chemical species may be used in some embodiments to dope the cooling fluid to specifically provide a relatively short T1 and T2 for said fluid, which can be useful in the context of imaging the thermal treatment using MRI. The concentration of the dopant can be controlled so that minimum interference with MRI signals from the prostate takes place, thereby improving the MRI imaging and thermometry operations.

In some embodiments, the dopant is adjusted so that little or no signal occurs from the cooling liquid for echo times greater than about 7 milliseconds, and consequently few visible flow, motion or "ghosting" artifacts interfere with the MRI imaging of the prostate. However, echoes less than or equal to about 7 milliseconds can still be used to determine the positioning of the cooling apparatus accurately within the patient's body. This can be useful for localizer sequences as part of the planning and execution of the thermal treatment. In some embodiments, the dopant would be added to the cooling fluid prior to deployment in the cooling apparatus to minimize or eliminate artifacts in the MRI imaging of the treatment zone and surrounding volume.

Figure 3:
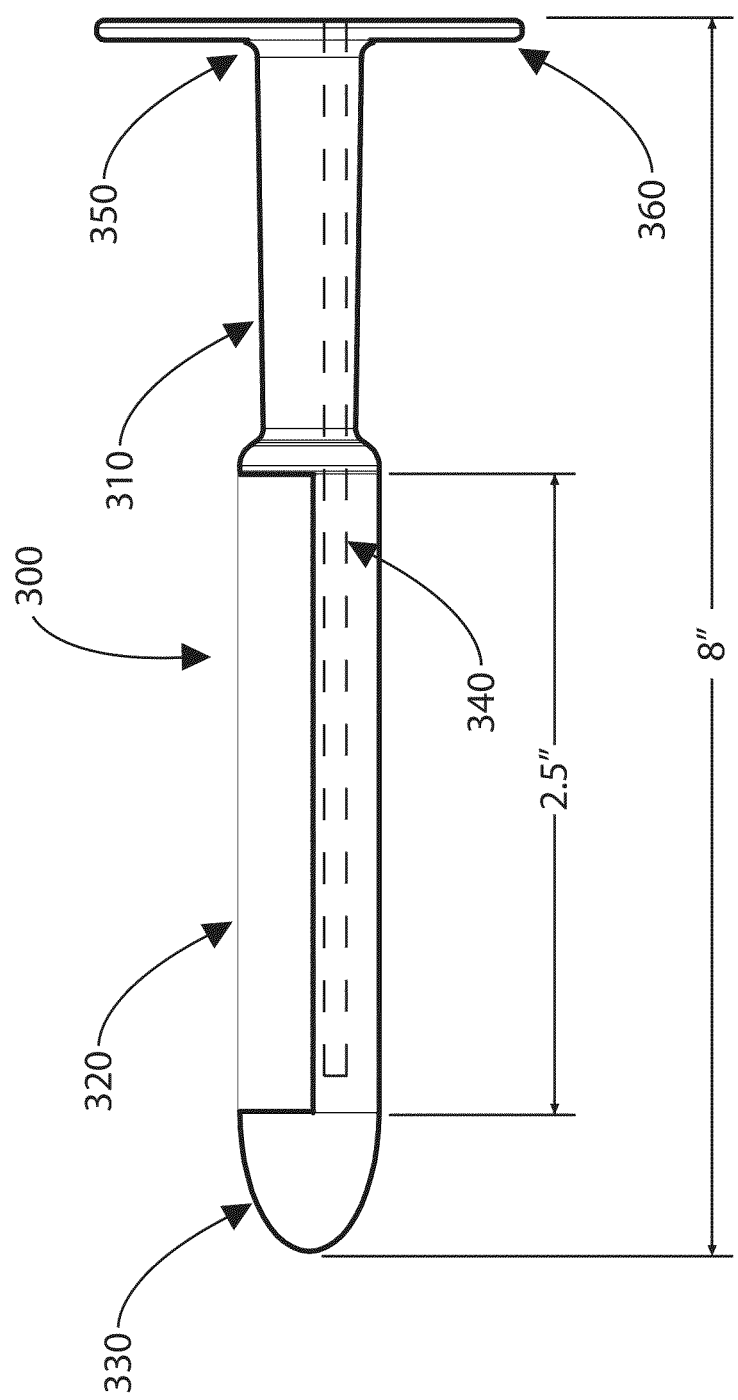
FIG. 3 illustrates a side view of an exemplary cooling apparatus and illustrative dimensions thereof.

FIG. 3 illustrates a cooling apparatus 300 consistent with the present discussion, and in some examples being similar to that described above with regard to FIG. 2. In the shown example, the cooling apparatus 300 is approximately 8 inches long to facilitate insertion into a patient body cavity, e.g., the rectum, to a depth sufficient to reach the vicinity of the thermal treatment volume, e.g., near the prostate. In some embodiments the cooling apparatus 300 is generally circular in cross-section as will be described in more detail below. In some embodiments, the cooling apparatus comprises a first tip end 330 which is inserted into the patient, and a second end 350 which may extend outside the patient's body in use. A cooling portion 320 of cooling apparatus 300 can, in some embodiments, be about 2.5 inches long and about 0.9 inches in diameter. These dimensions can be adjusted as would be understood by those skilled in the art, and in some embodiments different lengths of the cooling apparatus 300 and different lengths of the cooling portion 320 could be used to suit the size and shape of individual patients. Similarly, the cooling portion 320 has a diameter in some embodiments ranging between 0.25 and 2.0 inches according to the size and shape of the patient and/or the nature and proximities of the treatment volume and the surrounding tissues to be protected.

The drawings provided are not drawn to scale, but given for the purposes of illustration.

As discussed, the cooling apparatus 300 also includes an elongated member 310 and through which runs the cooling fluid plenum 340 and sensor wires and other components mentioned earlier.

A handle or similar mechanical extension 360 is provided and secured to cooling apparatus 300 to allow an operator or machine to control the position and/or movement of cooling apparatus 300. Also, such handle or mechanical extension 360 can prevent inadvertent over-insertion of cooling apparatus 300 into the patient and, when firmly attached to a positioning system on the MRI table, serves to reduce patient motion.

Figure 4:
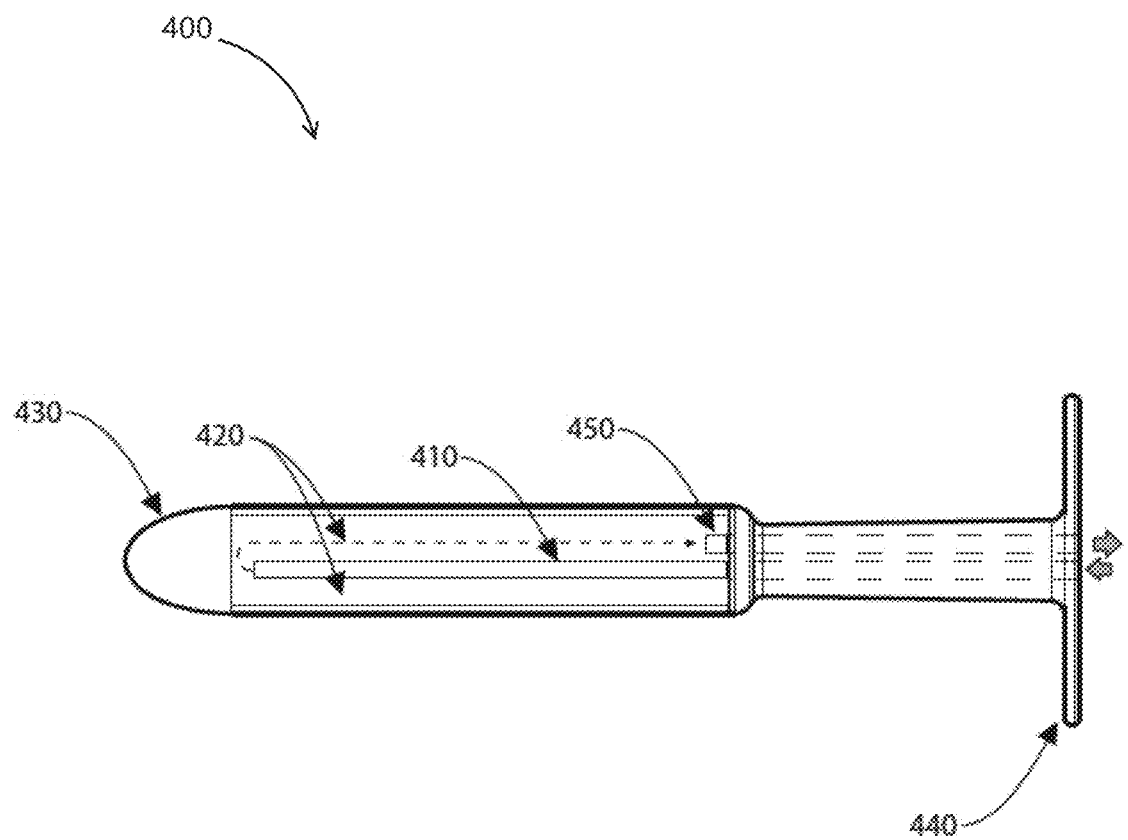
FIG. 4 illustrates a plan view of an exemplary cooling apparatus.

FIG. 4 illustrates a plan view of a cooling apparatus 400 similar to those described above. Cooling apparatus 400 includes a first flow path 410 for moving a cooling fluid along a first direction, e.g., into the apparatus, towards the tip end 430 of the apparatus. Cooling apparatus 400 also includes a second flow path 420 for moving the cooling fluid in a second direction, e.g., out of the apparatus, through other plenums 450 towards the second (or base) end 440.

Figure 5:
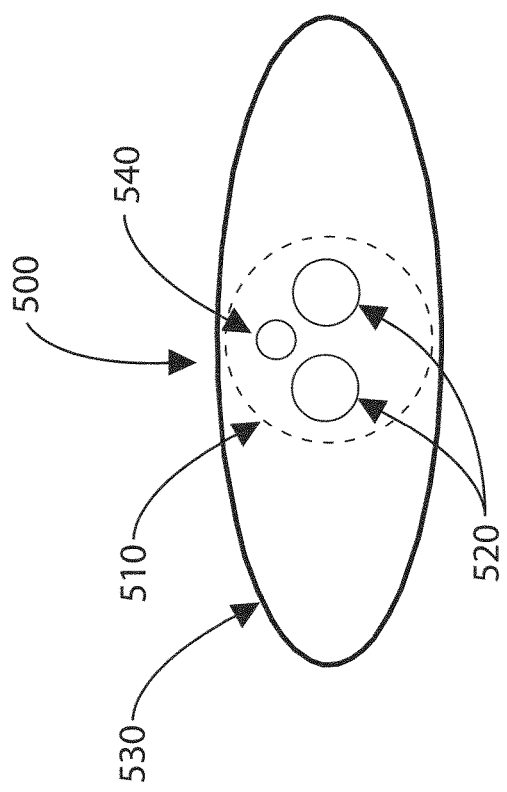
FIG. 5 illustrates a cross-section of an exemplary simplified cooling apparatus.

FIG. 5 illustrates an exemplary cross-section near the external portion of a cooling apparatus 500 according to one or more embodiments hereof. An outer shell, e.g., a thin plastic shell is shown by 510, which has a substantially circular cross-section, but said cross-section being adaptable for the purpose and use intended and the shape of the space into which the apparatus body 530 is to be inserted.

The cooling apparatus 500 includes internal components as described herein, including at least one set of fluid ingress-egress ports and channels 520 through which the cooling fluid can move into and out of the cooling apparatus 500, carrying with it heat energy deposited in to the tissue proximal to the cooling apparatus, particularly the rectal wall near the thermal treatment volume.

Temperature sensors and other electrical elements can run through the cross-section of the cooling apparatus 500 in an internal tube 540 used to house, isolate, insulate, and protect various sensors and their connections. In some embodiments, internal tube or tubes 540 are disposed to position their active thermal sensors appropriately within the cooling apparatus 500 to measure, for example, temperature adjacent to the rectal wall disposed towards the thermal treatment volume.

In some embodiments, the rates of flow into and out of said cooling apparatus are the same or approximately the same for incompressible fluids. In some embodiments, the temperature of the cooling fluid entering said cooling apparatus is lower than that of the cooling fluid exiting said cooling apparatus, as the fluid acquires some thermal energy while it is in or around the cooling portion of a cooling apparatus and near the thermal treatment zone of the patient. The tubing carrying the flowing cooling fluid can be made of a large number of materials and dimensions, depending on the application at hand. In some embodiments, the cooling fluid internal to the cooling apparatus flows through tubing made from metal which is not susceptible to magnetic fields in a MRI imaging magnet environment, nor does said metal cause significant MRI image artifacts.

In other embodiments, the temperature of the cooling fluid is monitored in at least one location. For example, the temperature of the fluid is monitored at or around its entrance to the cooling apparatus and/or at or near the exit from the cooling apparatus. The rate of heat removal is calculated in some embodiments. In other embodiments, a control system is provided for controlling a rate of flow and a temperature, or a pressure or another parameter of the cooling fluid at least at one location thereof. In one example, a maximum cooling fluid temperature is determined above which an alarm or other event is triggered to take place, including shutting off or reducing the power available to the heating portion of the thermal treatment apparatus.

More than one temperature sensor can be used in the cooling apparatus. For example two, four, or another number of sensors can be disposed at key locations at or near the walls of the cooling apparatus to monitor temperature distributions and trends. In some embodiments, some or all of the temperature sensors are MRI-compatible, and can provide both a baseline body temperature prior to cooling and dynamic temperatures of the cooling fluid once the treatment is underway.

Figure 6:
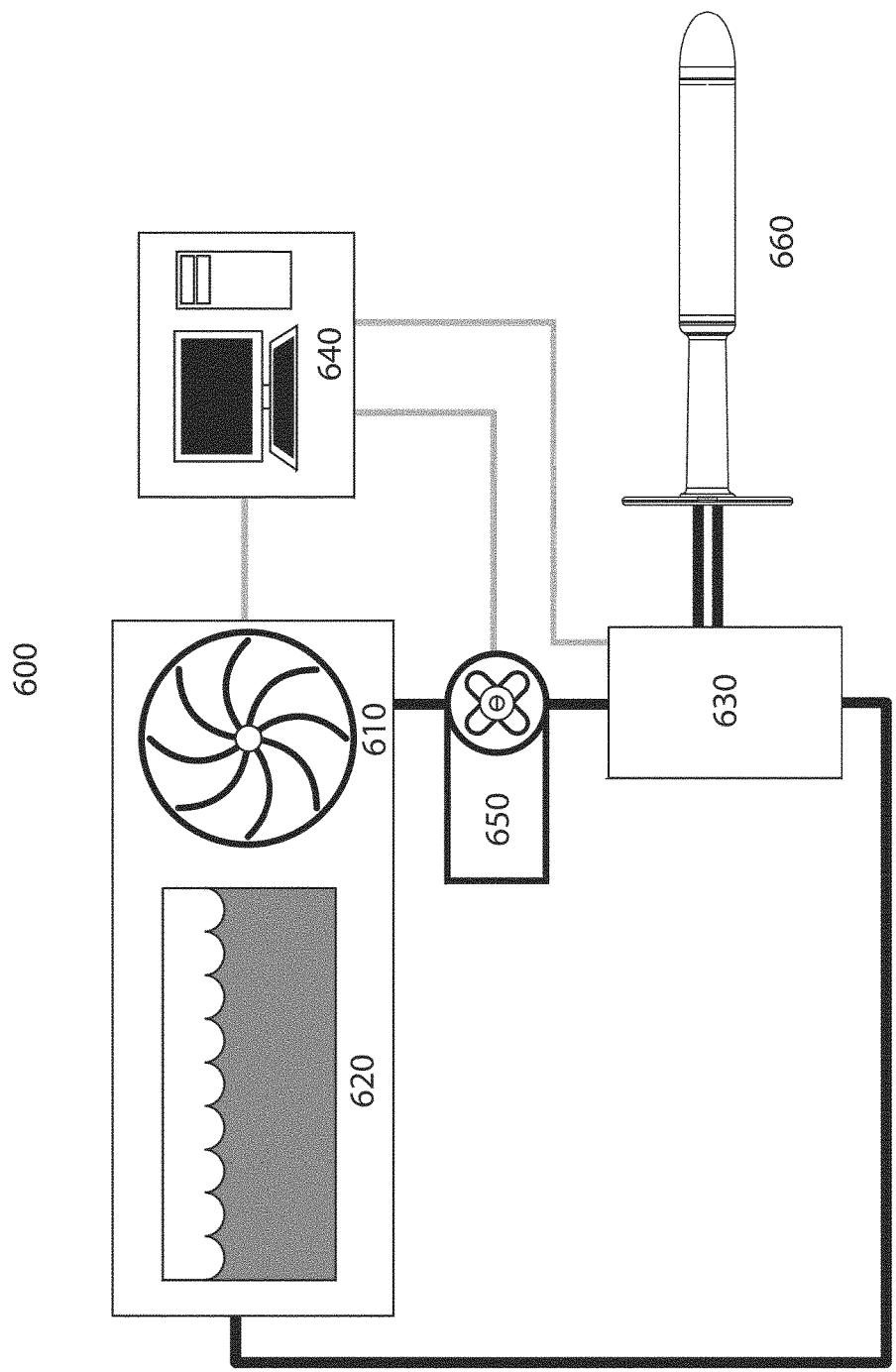
FIG. 6 illustrates an exemplary system including a cooling apparatus and fluid control apparatus.

In further embodiments, as illustrated in FIG. 6, a circulation system 600 is provided and coupled to the cooling fluid within the cooling apparatus 660. This may include a pump 610 for pumping (or driving) the cooling fluid through the cooling apparatus. An electrically-powered pump, a peristalsis pump, or other type of pump may be used to move the fluid. Also, in some embodiments, a filter and/or heat exchanger can be provided for filtering or cooling the cooling fluid within a reservoir 620 coupled to the fluid supply of the cooling apparatus.

In some embodiments, a bypass 630 is provided for the cooling fluid in addition to the flow-through mode so that the fluid bypasses the cooling apparatus and does not flow, or flows in closed loop circulation in a reservoir-pump circuit 610 and 620 without moving through the cooling apparatus. This can be useful to obtain a baseline temperature measurement with MRI prior to starting treatment or, after treatment, if no further cooling of the areas adjacent to the cooling apparatus is required. In some embodiments an operator or a control system 640 automatically determines whether to employ flow-through operation (cooling fluid moves through the cooling apparatus) or bypass mode of operation. In yet other embodiments, a throttle valve 650 or distribution element is used to vary the flow rate of fluid passing through the cooling apparatus. The variability thereof being adjustable between an upper and a lower bound. Said upper bound of flow through the cooling apparatus being fully flow-through and said lower bound of flow through the cooling apparatus being fully bypass in some embodiments. In other embodiments some percentage flow rates are chosen as the upper and lower bounds respectively.

Those skilled in the art would appreciate the aspects described above, including that providing an appropriate chemical or contrast agent or isotope can render the flow of said cooling fluid visible or invisible to MRI as desired. In some embodiments, the cooling fluid is rendered substantially invisible to the MRI imaging system in use so that few or no artifacts from the flow of the cooling fluid are seen. The dopant can be selected so that it is not toxic for use in patient environments where there is a risk of leakage of fluid coming into contact with the patient or practitioners. The doping of the cooling fluid can improve the accuracy of the thermometry in nearby tissues and organs in the context of MRI-monitored treatments and MRI-based temperature measurements. By obtaining increased accuracy in real-time temperature measurements of the treatment volume, more effective and efficient and faster treatments can be obtained.

Those skilled in the art will also understand that the present disclosure and examples would be of use in transrectal treatments of the prostate and not only for transurethral treatment of the prostate. Likewise, treatment of tissues in or beside body cavities such as those in the respiratory or sinus or digestive or cardiac systems can also benefit from the present apparatus, system, and methods for use of the same. Some of the present disclosure and examples could also be used in thermal therapy treatments of solid tissues such as brain or breast.

The present invention should not be considered limited to the particular embodiments described above, but rather should be understood to cover all aspects of the invention as fairly set out in the attached claims. Various modifications, equivalent processes, as well as numerous structures to which the present invention may be applicable, will be readily apparent to those skilled in the art to which the present invention is directed upon review of the present disclosure. The claims are intended to cover such modifications.

We claim:

1. A cooling apparatus for insertion into a patient aperture for cooling healthy tissue proximal to diseased tissue undergoing thermal therapy, the apparatus comprising:
   a housing of a predetermined shape and size and having opposing first and second ends, the housing constructed of a material having an acoustic impedance matched to a cooling fluid so as to minimize reflection and scattering of incident therapeutic ultrasound radiation, said housing material further being compatible with magnetic resonance imaging so as to minimize magnetic resonance imaging artifacts;
   a cooling portion of said housing disposed proximal to said first end of the housing, the cooling portion including an internal fluid reservoir for holding the cooling fluid passed through said apparatus;
   the first end of said housing further having a first taper to facilitate insertion of the first end of the apparatus into said patient aperture;
   an internal isolation tube that extends from the first end to the second end of the housing;
   an elongated section of said housing disposed proximal to said second end of the housing, said housing having a mechanical extension secured to the second end of the housing, said mechanical extension configured to stop said apparatus from being over-inserted into said patient aperture;
   the second end of the housing having a fluid ingress port for receiving the cooling fluid to be provided to said cooling portion of the apparatus and a fluid egress port for receiving the cooling fluid from said cooling portion of the apparatus; and
   a plenum that extends into said internal fluid reservoir and is defined by walls disposed radially inward of the cooling portion inner walls defining said internal fluid reservoir, the plenum in fluid communication with the fluid ingress port to receive the cooling fluid therefrom and in fluid communication with the internal fluid reservoir to provide the cooling fluid thereto,
   wherein the cooling portion includes inner walls defining the internal fluid reservoir.

2. The apparatus of claim 1, said housing being adapted in shape and size for inclusion into a rectal cavity of the patient for use in conjunction with a thermal therapy applied to a prostate of said patient.

3. The apparatus of claim 2, the housing having a construction compatible with ultrasonic thermal therapy of the prostate, and further compatible with magnetic resonance imagining of a region of the patient in the proximity of said prostate.

4. The apparatus of claim 1, said cooling fluid suitable for use with said thermal therapy and further suitable for use with said magnetic resonance imaging.

5. The apparatus for claim 4, further comprising a dopant substance within said cooling fluid to enhance a function of said magnetic resonance imaging.

6. The apparatus of claim 4, further comprising a dopant substance within said cooling fluid to reduce an imaging artifact of said magnetic resonance imaging.

7. The apparatus of claim 1, further comprising a temperature sensor disposed in the internal tube proximal to the second end of the housing.

8. The apparatus of claim 7, said temperature sensor configured and positioned to monitor a temperature of said cooling fluid within said apparatus.

9. The apparatus of claim 1 further comprising a fluid ingress channel and a fluid egress channel through which the cooling fluid can move into and out of the cooling apparatus, the fluid ingress channel in fluid communication with the fluid ingress port, the fluid egress channel in fluid communication with the fluid egress port.

10. The apparatus of claim 1 wherein the mechanical extension comprises a handle.

11. The apparatus of claim 1, wherein the cooling portion has a diameter of 0.25 inches to 2.0 inches.

12. The apparatus of claim 11, wherein the cooling portion has a diameter of 0.9 inches.

13. The apparatus of claim 1, wherein the cooling portion is 2.5 inches long.

14. The apparatus of claim 1 wherein the internal isolation tube having a temperature sensor therein, in which the temperature sensor is disposed radially inward of the cooling portion inner walls defining said internal fluid reservoir.

15. The apparatus of claim 14 wherein the internal isolation tube isolates the temperature sensor from the cooling fluid.

16. The apparatus of claim 14 wherein the walls defining the plenum and the side walls of the internal isolation tube are spaced radially inward from and do not contact the cooling portion inner walls defining said internal fluid reservoir.

17. The apparatus of claim 1 wherein the plenum is a first plenum, the apparatus further comprising a second plenum that is separate from the first plenum, extends into said internal fluid reservoir and is defined by walls disposed radially inward of the cooling portion inner walls defining said internal fluid reservoir, the second plenum in fluid communication with the internal reservoir to receive the cooling fluid therefrom and in fluid communication with the fluid egress port to provide the cooling fluid thereto.

18. The apparatus of claim 17 wherein the walls defining the first plenum and the side walls of the internal isolation tube are spaced radially inward from and do not contact the cooling portion inner walls defining said internal fluid reservoir.

19. The apparatus of claim 18 wherein the walls defining the second plenum are spaced radially inward from and do not contact the cooling portion inner walls defining said internal fluid reservoir.

20. The apparatus of claim 19 wherein the internal isolation tube isolates the temperature sensor from the cooling fluid.

21. A method comprising:
inserting the cooling apparatus of claim 1 into a rectum of a patient; and
using the cooling apparatus to cool a region of the rectum in proximity to a prostate of the patient while the prostate of the patient undergoes thermal therapy.

22. A method comprising:
inserting the cooling apparatus of claim 14 into a rectum of a patient; and using the cooling apparatus to cool a region of the rectum in proximity to a prostate of the patient while the prostate of the patient undergoes thermal therapy.

* * * * *